United States Patent
Plato et al.

(10) Patent No.: US 7,402,302 B2
(45) Date of Patent: Jul. 22, 2008

(54) COMPOSITION OF GRANDLURE AND DICHLORVOS FOR ATTRACTING AND KILLING BOLL WEEVILS IN BOLL WEEVIL TRAPS

(76) Inventors: Thomas Alfred Plato, 2001 Holcombe, #3501, Houston, TX (US) 77030; James Clayton Plato, 11803 Warwickshire Ct., Houston, TX (US) 77077; James Scott Plato, 2104 Shoal Lake Ct., League City, TX (US) 77573; Stacy Elizabeth Plato, 2001 Holcombe Blvd. #203, Houston, TX (US) 77030; Timothy Bruce Johnson, 602 Hill Ave., Langhorne, PA (US) 19047

( * ) Notice: Subject to any disclaimer, the term of this patent is extended or adjusted under 35 U.S.C. 154(b) by 177 days.

(21) Appl. No.: 10/752,801

(22) Filed: Jan. 7, 2004

(65) Prior Publication Data

US 2005/0147634 A1    Jul. 7, 2005

(51) Int. Cl.
*A01N 25/34* (2006.01)
(52) U.S. Cl. .................. 424/84; 43/132.1; 424/405; 424/406; 424/409; 514/144; 514/703; 514/729
(58) Field of Classification Search .................. None
See application file for complete search history.

(56) References Cited

U.S. PATENT DOCUMENTS 2,775,994 A * 1/1957 Rowe .................. 264/74
3,888,830 A * 6/1975 Ogasawara et al. ........... 522/37
4,160,335 A * 7/1979 Von Kohorn et al. .......... 43/131
5,413,784 A * 5/1995 Wright et al. .............. 424/93.5
5,759,561 A * 6/1998 Angst et al. ................. 424/407
6,183,733 B1 * 2/2001 McKibben ................... 424/84

* cited by examiner

*Primary Examiner*—Neil Levy
(74) *Attorney, Agent, or Firm*—Defillo & Associates Inc; Evelyn A. Defillo

(57) ABSTRACT

Compositions and methods for attracting, capturing and killing populations of cotton boll weevils (*Anthonomus grandis Boh.*) in boll weevil traps are disclosed. With respect to the attraction and capture of boll weevils with Grandlure, the synthetic pheromone of the cotton boll weevil, there is generally an increased number of boll weevils captured in the trap cylinder when an insecticide dispenser is included in the trap cylinder to kill the weevils and thus prevent their escape. Additionally, dead boll weevils are more accurately counted than live boll weevils. The compound dichlorvos (2,2-dichlorovinyl dimethyl phosphate or DDVP) is the most preferred among those few insecticides that can be used in traps for killing and preventing weevil escapes. This is also the preferred insecticide when combined with Grandlure in a single dispenser to kill boll weevils or inhibit their ability to develop normally and reproduce. The single Grandlure dichlorvos dispenser provides for significant savings in labor expenses in large area trapping and eradication programs and significantly reduces the disposal of waste materials from spent dispensers.

8 Claims, No Drawings

COMPOSITION OF GRANDLURE AND DICHLORVOS FOR ATTRACTING AND KILLING BOLL WEEVILS IN BOLL WEEVIL TRAPS

BACKGROUND OF THE INVENTION

1. Field of the Invention

This invention involves slow release delivery systems for use in the monitoring and the control of cotton boll weevils and other insects that over-winter or inhabit crop and nearby non-crop areas where host crops are present and not present.

2. Description of the Art

Boll weevils are coleopteran insects that feed on cotton plants; causing serious damage to the plants and reducing yield. As a consequence, multiple applications of insecticides are required to maintain populations below economically damaging thresholds. Boll weevils are generally found in cotton growing regions of North, Central, and South America.

All life stages except the adult stage are spent inside cotton squares or bolls. Male boll weevils release an aggregating pheromone after feeding on cotton squares and both males and females are attracted to this pheromone. In general, adult, over-wintered females feed for 3 to 7 days, mate with males and start laying eggs. Starting in the spring, females lay one egg per square, but at the end of the crop lay several in a boll. Each female usually lays an average of 150 eggs in her lifetime, each of which hatch in about three to five days. The resulting grubs or larvae feed about a week inside squares or bolls before changing into pupae; this stage lasts three to five days. Adults develop from pupae and cut their way out of squares or bolls. New adults feed from three to five days, mate, and begin laying eggs for the next generation. These cycles are repeated during the season until the cotton plants are either destroyed or killed by frost. It is estimated that a single pair of weevils, left uncontrolled, can generate up to two million offspring per year.

The boll weevil is a non-indigenous pest to the United States and there have been active programs to eradicate the boll weevil from the United States for more than twenty years. Currently there are about 12.5 million acres in active eradication programs, about four million acres in post-eradication programs and 300,000 acres in pre-eradication zones. The eradication programs have been financed by federal and state government funding and producer fees. Upon completion during the next 10 years, the total cost of these programs will have exceeded $2.5 billion. The eradication programs use special traps to monitor populations of boll weevils, to determine when cotton fields are to be treated with insecticide for killing boll weevils, and to eliminate very low populations of boll weevils. The traps typically include separate dispensers of Grandlure (a synthetic, four component version of boll weevil aggregation pheromone) to attract and dispensers of dichlorvos (DDVP) to kill trapped weevils. Dichlorvos prevents most of the weevils trapped in the capture cylinder of the trap from escaping and dead weevils are more easily tabulated when the trap is serviced than are live weevils.

Examples of boll weevil attractant compositions including Grandlure are described, for example, in U.S. Pat. No. 3,803,303. Grandlure has been used in combination with feeding stimulants, poisons and other compounds, in a variety of different types of devices, for example, those described in U.S. Pat. No. 4,027,420. Polymeric compositions for attracting boll weevils using a sex attractant in combination with polyethylene glycol and a toxicant such as p-dichlorobenzene are disclosed, for example, in U.S. Pat. No. 3,803,303. The contents of these patents are hereby incorporated by reference. Plant attractants such as caryophylline oxide and beta-bisabalol have been used in some of these devices, where the attractant is applied to cotton dental-rolls. Other controlled-release dispensers have been developed to give long-term release of Grandlure (McKibben and Davich, Environmental Entomology, 6(6):804-806 (1977). Volatile compounds present in the cotton plant have been shown to attract boll weevils, although not when they are diapausing. Grandlure has been used in combination with volatile compounds present in dead plan material, such as described in U.S. Pat. No. 6,183,733.

Examples of a cotton boll weevil trap suitable for use with this invention are described, for example, in U.S. Pat. No. 6,430,868. The content of this patent is hereby incorporated by reference.

The pheromone and dichlorvos dispensers should each be dated and replaced on a regular basis (each 7 to 28 days) throughout the growing season in traps that are deployed from 1 per acre to 1 per 10 acres. The labor required for replacing and disposing of each type of dispensers is a significant cost to eradication programs. In an average year of an active eradication program on 12,500,000 acres, an estimated 160 metric tons of spent dispensers are collected from traps for disposal in landfills.

SUMMARY OF THE INVENTION

The present invention is directed to a composition for attracting and killing weevils that damage and destroy plants.

Compositions, devices and methods for attracting cotton boll weevils, capturing and killing them or rendering that portion of a population infertile are disclosed. With respect to the cotton boll weevil, the compositions include a pheromone for boll weevils, preferably Grandlure, and also include a toxicant, such as but not limited to dichlorvos (DDVP). Compositions including these components can be used year-round to attract and kill boll weevils but are particularly effective when boll weevils are migrating into or out of cotton fields. The pheromone component of the invention can also be altered to attract other weevil species including but not limited to pecan weevil, pepper weevil, citrus root weevil, sweet potato weevil, rice water weevils and other similar pests.

The compositions can be used in traps such as those commonly used to attract boll weevils or other insects. An example of such a trap is described in U.S. Pat. No. 6,430,868.

In one embodiment, the components are included in polymer-based compositions that release the active components over a sustained period of time. The devices can be used to attract and kill cotton boll weevils, thereby monitoring populations in cotton fields and contributing to the control and eradication of such populations. Generally, the traps and devices are set out in a perimeter pattern around a cotton field and the boll weevils are attracted to the traps by the Grandlure and are killed by the dichlorvos.

In accordance with this discovery, it is an object of the invention to provide a composition that has an attractant and toxicant for weevils, particularly boll weevils.

Another object of the invention is the provision of the composition as detection, surveying, monitoring, or control agent for weevils.

A further object of the invention is to reduce the disposal problem by 50% or 80 metric tons.

An even further object of this invention is to cut the labor cost of servicing (opening packages, date writing on each dispenser, depositing the dispenser in a capture cylinder and disposing of the dispenser) an estimated four million traps by an approximate 500,000 hours or $2,500,000 per eradication year.

A still further object of the invention is to use a single device that has a composition containing both an attractant and toxicant, which is economically and environmentally advantageous.

Other objects and advantages of the invention will become readily apparent from the ensuing description.

DETAILED DESCRIPTION OF THE INVENTION

The present invention discloses compositions, devices and methods for attracting and killing or rendering infertile populations of cotton boll weevils and other insect species.

The compositions and methods described herein can be used in diapause and in-season control programs for cotton boll weevil populations. An effective diapause control program can lessen the total number of insecticide applications needed in the following season for maximum protection from boll weevils and create favorable conditions for eliminating weevils as pests of economic importance. Such a program can minimize the destruction of beneficial insects that suppress economically damaging lepidoptera, spider mites, aphids and other harmful insects and ultimately contribute to the eradication of the boll weevil from extensive cotton growing regions.

I. Compositions

A. Pheromones

With respect to the cotton boll weevil, the compositions preferably also include an effective, boll weevil attracting amount of Grandlure or an effective analogue thereof, or the natural boll weevil pheromone. With respect to other over-wintering insects, pheromones for many insects are known or can be readily identified.

Grandlure is a synthetic boll weevil pheromone, and is extremely effective at attracting boll weevils. Grandlure consists of four components designated Grandlure I (IR-(Z)-1-methyl-2-(1-methylethenyl)cyclobutane ethanol), Grandlure II ((Z)-2-(3,3-dimethylcyclohexylidene)ethanol), Grandlure III ((Z)-(3,3-dimethylcyclohexylidene)acetaldehyde) and Grandlure IV ((E)-(3,3-dimethylcyclohexylidene)acetaldehyde). In preferred embodiments of the invention, the ratio of the four components of Grandlure are 30% Grandlure I, 40% Grandlure II, 15% Grandlure III, and 15% Grandlure IV. Grandlure is known to be effective at doses of approximately 10 mg of Grandlure per trap every 14 days. Grandlure greater than 10 mg per dispenser can be used to increase the longevity of the invention to greater than 14 days. In preferred embodiments of the invention, 10 mg of Grandlure is combined with 60 mg of dichlorvos for replacement every 14 days or 25 mg of Grandlure is combined with 90 mg of dichlorvos for replacement every 28 days. As the weevil population is reduced, the pheromone becomes increasingly effective at "calling" weevils to the trap. Continuous trapping helps determine the treatment efficacy. An effective amount of Grandlure depends upon multiple factors including the size and layout of the cotton field, the size and location of over-wintering habitat, and the size of the population of boll weevils being trapped.

Other insect pheromones can be used for other important pests, including but not limited to, pepper weevil, pecan weevil, citrus root weevil, sweet potato weevil and rice water weevil.

B. Insecticides

Any insecticide known to be effective at killing boll weevils or other over-wintering insects can be used. Suitable insecticides effective at killing these insect populations are well known to those skilled in the art, and include organophosphates such as dichlorvos (DDVP) and naled, carbamates such as propoxur and pyrethroids. Preferred insecticides are those which are approved by the Environmental Protection Agency for example, in the case of boll weevils, for use on cotton or are approved for use in insect traps. Insecticides that are toxic to boll weevil such as, dichlorvos (DDVP), naled, propoxur, malathion, azinphosmethyl, methyl parathion and any of the various pyrethroid compounds, which are commercially available, are preferred insecticides. Dichlorvos (DDVP) is currently the preferred insecticide due to its characteristic of producing a vapor toxic to boll weevils trapped within a capture cylinder. Some biological insecticides are known which are effective at killing the boll weevil and biological insecticides are also known for a variety of other over-wintering insect populations. U.S. Pat. No. 5,413,784 describes a useful bio-pesticide with activity against the boll weevil; the bio-pesticide is an entomopathogenic fungus, *Beauveria bassiana*, preferably *Beauveria bassiana*, ATCC-74040 (ARSEF-3097). By using the microbe or fungus, or mutants thereof, boll weevils can be controlled without the environmental and public safety hazards presented by chemical control agents.

C. Optional Components

The compositions can include additional optional components. These components include attractants other than the pheromones, insect growth regulators, and insect sterilants.

II. Traps Including the Composition

The compositions can be used in traps such as those commonly used to attract boll weevils. Such traps are well known to those skilled in the art, and are commonly used in many states in their boll weevil eradication programs. An example of such a trap is described in U.S. Pat. No. 6,430,868. The traps are typically plastic, yellow-green fluorescent traps that are highly visible around cotton fields. The color of the trap is effective at attracting boll weevils, in addition to the compositions placed inside the traps.

In one embodiment, the trap is an inverted cup, topped with a cone-shaped plastic mesh screen. A clear plastic capture chamber on top of the cone contains a dispenser for the boll weevil attractant and insecticide composition. The trap can be placed in a location where boll weevils may be present, and when the trap includes an effective amount of the compositions described herein, boll weevils are attracted to the trap. The boll weevils are attracted by the combination of the daylight fluorescent yellow-green color of the trap and the Grandlure within the compositions described herein, and move upwardly on the trap into a perforated collecting or trapping cylinder at the upper location or end of the trap.

The insecticide component of the invention, preferably dichlorvos, kills the weevils by direct contact with the device and through vapor action thus preventing their escape and aiding in accurately counting the captured insects. Initially these traps may be placed from 100 to 250 feet apart around the edge of a cotton field. After eradication, the cotton fields can be monitored, for example, with the equivalent of 1 trap for every 10 acres.

Those of skill in the art can readily adapt the boll weevil traps for use in controlling populations of other over-wintering insects.

II. Polymer-based Insecticide Compositions

In one embodiment, the compositions are included in polymer-based insecticide compositions that are impervious to environmental conditions and that release the Grandlure or other pheromone and dichiorvos or other insecticide over a period of time. Such compositions typically include a polymer or co-polymer of plastic, Grandlure or an equivalent pheromone, and an insecticide such as dichlorvos. The devices are typically formed into flat sheets, solid pellets, laminated sheets rectangular or square dispensers compounded, matrix, laminated or sandwiched, with the compositions described herein. In the preferred embodiments, dichlorvos continually migrates to the surface of the device and vaporizes. Dichlorvos is capable of killing boll weevils by its vapor action but it can take up to one hour for mortality to occur. By combining Grandlure with dichlorvos into a single device, cotton boll weevils are more likely to come into direct contact with the lure resulting in a greater dosage to the weevil and a higher percentage of insect mortality before weevils can escape from the capture cylinder.

In one preferred embodiment, polyvinylchloride-acrylic copolymer is blended with plasticizers such as phthalate ester and butyl benzyl phthalate and a thickener such as silicon dioxide. Grandlure is added to the mixture to yield a final concentration of 0.83% and dichlorvos is added to the mixture to yield a final concentration of 5%. In the sheet molding process, the mixture is poured to form a thin sheet that is cured in an oven at 100 to 300 degrees F. to achieve a solid matrix capable of a controlled slow release of the pheromone and dichlorvos. The cured sheets can be cut to any size desired for use in boll weevil traps. The Grandlure attracts the boll weevils into the trap chamber wherein the dichlorvos kills the weevils through contact and vapor activity. When cut into squares weighing 1.2 grams, the lure contains 10 mg of Grandlure and 60 mg of dichlorvos.

In a second preferred embodiment, polyvinylchloride-acrylic copolymer is blended with plasticizers such as phthalate ester and butyl benzyl phthalate and a thickener such as silicon dioxide. Grandlure is added to the mixture to yield a final concentration of 2.1% and dichlorvos is added to the mixture to yield a final concentration of 7.5%. In the sheet molding process, the mixture is poured to form a thin sheet that is cured in an oven at 100 to 300 degrees F. to achieve a solid matrix capable of a controlled slow release of the pheromone and dichlorvos. The cured sheets can be cut to any size desired for use in boll weevil traps. The Grandlure attracts the boll weevils into the trap chamber wherein the dichlorvos kills the weevils through contact and vapor activity. When cut into squares weighing 1.2 grams, the lure contains 25 mg of Grandlure and 90 mg of dichlorvos.

IV. Methods for Monitoring and Controlling Boll Weevil Populations Using the Compositions The traps as described herein can be set at any time of the year. The density of traps is related to the population of boll weevils and the objective of using the monitoring traps. In eradication programs traps are used at the rate of one trap for every 1-4 acres of cotton planted. In post-eradication uses, monitoring traps may be used at the rate of one trap for every 10-40 acres of cotton or they can be placed along possible entries of migration or accidental introduction such as major highways. The efficacy of the trap for controlling boll weevils can be aided by other farming practices designed to reduce the amount of food available to boll weevils. These practices include zone-wide concentrated plating dates, planting early maturing cotton varieties, and destroying cotton stalks immediately after harvest to prevent re-growth. These methods can be readily adapted for use in controlling insect populations other than boll weevils.

The invention will be further understood with reference to the following non-limiting examples.

EXAMPLE 1

Response of Dispersing Boll Weevils to Grandlure Plus Dichlorvos (DDVP)

A study was conducted in Willacy County in Texas. Traps were baited with a single polyvinyl chloride acrylic-copolymer device (a.k.a. "Combo Lure") containing 10 mg of Grandlure and 60 mg of dichlorvos and compared to traps containing two separate dispensers, one containing 10 mg of Grandlure and one with 90 mg of dichlorvos (DDVP). The study was conducted on ten separate cotton fields with five traps of each treatment located at 100-foot intervals along the perimeter of each field. The order of trap placement was randomly chosen. The Combo Lure was replaced every 14 days. In the conventional two dispenser traps, the Grandlure dispenser was replaced every 14 days. The number of boll weevils captured in each trap was counted every 7 days for four weeks with a final count taken after 10 additional days. The results are shown below in Table 1.

TABLE 1

| Average number of boll weevils captured per trap per day | | | | | | |
|---|---|---|---|---|---|---|
| | Week | | | | | |
| | 1 | 2 | 3 | 4 | 5 | Total |
| Combo Lure (10 mg Grandlure + 60 mg dichlorvos) | 5.2 | 5.1 | 1.9 | 5.5 | 2.5 | 3.92 |
| Separate dispensers 10 mg Grandlure and 90 mg dichlorvos | 5.3 | 5.6 | 1.5 | 3.0 | 1.9 | 3.34 |

The Combo Lure that included both Grandlure and dichlorvos (DDVP) captured 17.4% more boll weevils than did the conventional system of having separate Grandlure and dichlorvos (DDVP) dispensers over the duration of the test. The difference in captured weevils was not statistically significant when analyzed by analysis of variance methods, but the lack of statistical difference is not considered to be relevant to the uniqueness of the invention. In addition to capturing a greater number of boll weevils, the Combo Lure took one-half the time to place in the trap than two separate dispensers and generated one-half the waste for disposal.

EXAMPLE 2

Response of Dispersing Boll Weevils to Grandlure Plus Dichlorvos (DDVP)

A study was conducted in Lamar and Red River Counties in Texas. Various lures that contained Grandlure and dichlorvos were evaluated. Lures with separate ingredients were also evaluated. The study was conducted on 10 cotton fields with five traps of each lure randomly placed along the perimeter of each field at 100-foot intervals.

TABLE 2

Average number of boll weevils captured per trap per day

|  | Week | | | |
| --- | --- | --- | --- | --- |
|  | 1 | 2 | 3 | Avg. |
| Combo Lure 10 mg (Grandlure + 60 mg dichlorvos) | 57.4 | 43.6 | 11.7 | 36.3 |
| Separate dispensers 10 mg Grandlure and 90 mg dichlorvos | 72.3 | 42.6 | 12.4 | 42.4 |

The Combo Lure that included both Grandlure and dichlorvos (DDVP) captured 14.4% fewer boll weevils than did the conventional system of having separate Grandlure and dichlorvos (DDVP) dispensers over the duration of the test. Again, the difference in captured weevils was not statistically significant when analyzed by analysis of variance and the lack of statistical difference is not considered to be relevant to the uniqueness of the invention. The Combo Lure took one-half the time to place in the trap than two separate dispensers and generated one-half the waste for disposal.

EXAMPLE 3

Release of Grandlure from Dispensers Containing both Grandlure and Dichlorvos (DDVP)

Dispensers used in examples 1 and 2 were placed in Plato Traps and exposed to ambient temperatures outside the Plato Industries facility in Houston, Tex. on Aug. 8, 2003. At days 0, 3, 7, 10, and 14, three dispensers of each treatment were removed from the traps, placed into sealed plastic bags and stored in a freezer for later analysis of chemical content. Samples were then analyzed for Grandlure content with a protocol whereby Grandlure was extracted with chloroform and alpha-terpineol and quantified utilizing gas chromatography. The amount of Grandlure released per dispenser per day was calculated by dividing the number of days in the sample period into the amount of Grandlure released. Dispensers containing both 10-mg of Grandlure and 60 mg of dichlorvos have release characteristics very similar to those containing 10 mg of Grandlure only (Table 3). The addition of dichlorvos did not substantially alter the release characteristics of the polyvinyl chloride-acrylic dispenser system and both dispensers released Grandlure over the desired 14-day period.

TABLE 3

Release rates of dispensers containing Grandlure and dichlorvos

|  | Average mg Grandlure released/dispenser/day Day | | | |
| --- | --- | --- | --- | --- |
| Dispenser contents | 0-3 | 3-7 | 7-10 | 10-14 |
| 10 mg Grandlure only | 1.27 | 0.70 | 0.53 | 0.15 |
| 10 mg Grandlure + 60 mg dichlorvos | 0.50 | 0.70 | 0.47 | 0.35 |

The invention as described by the specific embodiments is not meant to limit its scope. It is envisioned and apparent that many alternatives and variations may be encompassed by the present invention. It is intended that the spirit and scope of this disclosure include such alternatives and variations.

As to the manner of usage and operation of the present invention, the same should be apparent from the above description. Accordingly, no further discussion relating to the manner of usage and operation will be provided.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A composition for attracting and killing weevils comprising:
    a homogeneous mixture containing
    a polymer;
    an effective amount of weevil attracting pheromone;
    a plasticizer;
    a vapor releasing insecticide; and
    optionally a thickener;
    wherein the homogeneous mixture is formed into a hard solid matrix;
    wherein the insecticide is dichlorvos (DDVP);
    wherein the polymer is polyvinyl chloride acrylic copolymer, either compounded, matrix, laminated or sandwiched;
    wherein the active components of the mixture are released in the form of a vapor from the solid matrix over a sustained period of time.

2. The composition of claim 1 wherein the weevil pheromone is selected from the group of insect pheromones that attract boll weevils, pepper weevils, pecan weevils, citrus root weevils, sweet potato weevils and rice water weevils.

3. The composition of claim 1, wherein the weevil pheromone is Grandlure.

4. The composition of claim 1, further comprising an insect growth regulator or insect sterilant.

5. The composition of claim 1, wherein the plasticizer is butylbenzyl phthalate.

6. The composition of claim 1, wherein the thickener is silicon dioxide.

7. A composition of claim 1, wherein the solid matrix is cured between 100 to 300° F.

8. A composition for attracting and killing weevils consisting of:
    a homogeneous mixture consisting of:
    a polymer;
    an effective amount of weevil attracting pheromone;
    a vapor releasing insecticide;
    a plasticizer; and
    optionally a thickener;
    wherein the insecticide is dichlorvos (DDVP)
    wherein the polymer is polyvinyl chloride acrylic copolymer, either compounded, matrix, laminated or sandwiched;
    wherein the active components of the mixture are released in the form of a vapor from the solid matrix over a sustained period of time.

* * * * *